United States Patent
Evans et al.

(10) Patent No.: US 9,649,423 B2
(45) Date of Patent: May 16, 2017

(54) TREATMENT OF TRANSFUSION BLOOD

(71) Applicant: HAEMAFLOW LIMITED, Swansea (GB)

(72) Inventors: Alan Frederick Evans, Sutton Coldfield (GB); William Richard Johns, Reading (GB)

(73) Assignee: HAEMAFLOW LTD., Swansea (GB)

( * ) Notice: Subject to any disclaimer, the term of this patent is extended or adjusted under 35 U.S.C. 154(b) by 0 days.

(21) Appl. No.: 14/398,220

(22) PCT Filed: Apr. 25, 2013

(86) PCT No.: PCT/GB2013/051053
§ 371 (c)(1),
(2) Date: Oct. 31, 2014

(87) PCT Pub. No.: WO2013/164581
PCT Pub. Date: Nov. 7, 2013

(65) Prior Publication Data
US 2015/0086969 A1      Mar. 26, 2015

(30) Foreign Application Priority Data
May 1, 2012  (GB) .................................. 1207543.8

(51) Int. Cl.
| A61M 1/16 | (2006.01) |
| A61M 1/36 | (2006.01) |
| A61M 1/02 | (2006.01) |

(52) U.S. Cl.
CPC ........ *A61M 1/3627* (2013.01); *A61M 1/0272* (2013.01); *A61M 1/0281* (2013.01); *A61M 1/16* (2013.01); *A61M 1/369* (2013.01)

(58) Field of Classification Search
None
See application file for complete search history.

(56) References Cited

U.S. PATENT DOCUMENTS

| 3,579,999 | A | 5/1971 | Schwartz | |
| 6,087,087 | A * | 7/2000 | Yonetani | A61K 35/18 424/93.73 |
| 2012/0024156 | A1* | 2/2012 | Yoshida | A61M 1/0209 96/6 |
| 2012/0129149 | A1 | 5/2012 | Federspiel | |
| 2012/0225416 | A1 | 9/2012 | Yoshida | |
| 2013/0177524 | A1* | 7/2013 | Emanuele | A61K 31/765 424/78.31 |
| 2014/0353854 | A1* | 12/2014 | Johns | A61M 1/1698 261/74 |

FOREIGN PATENT DOCUMENTS

| EP | 0371178 | 6/1990 |
| WO | 03/066109 | 8/2003 |
| WO | 2011/014855 | 2/2011 |
| WO | 2011046841 | 4/2011 |
| WO | 2012/027582 | 3/2012 |
| WO | 2012/160347 | 11/2012 |
| WO | 2013164581 | 4/2013 |

OTHER PUBLICATIONS

International Search Report and Written Opinion, dated Jul. 2013, for PCT/GB2013/051053.
International Preliminary Report on Patentability for PCT/GB13/51053 dated Nov. 4, 2014.
F. J. W. Roughton et al., Accurate determination of O2 dissociation curve of human blood above 98.7% saturation with data on O2 solubility in unmodified human blood from 0 to 37 C; Depart of Celloid Science, Cambridge University Journal of Applied Physiology, vol. 35, No. 6, Dec. 1973.
John W. Severinghause, Simple, accurate equations for human blood O2 dissociations. J. appl. Physiol: Respirat. Environ. Exercise Physiol. Cardiovascular Research Inst and Dept, jweps@comcast.net, Abstract, 7 pgs, 46(3):599-602, 1979.

* cited by examiner

*Primary Examiner* — Ralph Gitomer
(74) *Attorney, Agent, or Firm* — Fleit Gibbons Gutman Bongini & Bianco PL; Paul D. Bianco; Gary S. Winer

(57) ABSTRACT

Blood is treated externally to a human or animal body, the blood having been extracted from a first human or animal body for delivery to a second human or animal body. The temperature and/or composition of the blood are controlled.

34 Claims, 1 Drawing Sheet

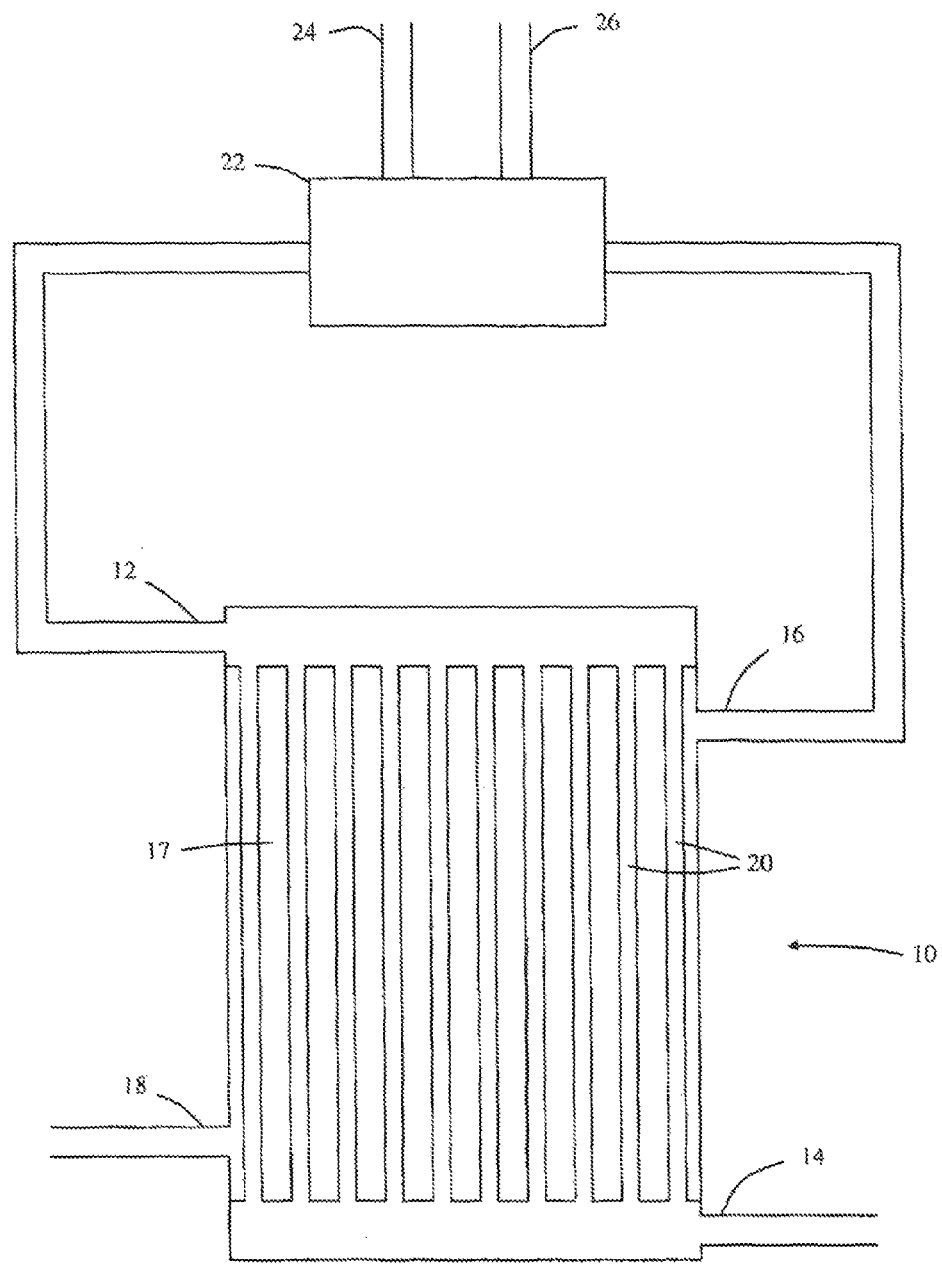

TREATMENT OF TRANSFUSION BLOOD

The present invention relates to methods for treating blood externally to the human or animal body, in particular to methods for controlling the properties of the blood.

Donated transfusion blood is venous blood that is relatively low in oxygen and high in carbon dioxide. The blood is typically citrated to improve its storage properties and prevent clotting in storage. At the point of delivery to the recipient, the blood should ideally be matched to the requirements of the recipient. For example, it may be desirable that it should closely approximate arterial blood. The problem in achieving these ideal properties is made more difficult because, whilst in storage between collection and use, the blood deteriorates. Deterioration in storage reduces the ability of transfused blood to carry oxygen around the body. In order to minimize deterioration in storage, widely used guidelines limit the storage of whole blood to 35 days and of red blood cells to 42 days. Even after relatively short periods in storage, it can take up to 48 hours in the body before transfused blood regenerates lost metabolites and is fully capable of carrying oxygen effectively. This shortcoming can be a particular problem where large blood transfusions are needed, particularly in patients with acute trauma or sepsis. Indeed, in a number of cases, the relatively inert transfused blood dilutes the remaining active blood in the patient's body to the extent that it reduces the ability of the blood to carry oxygen. The patient may then become more ill, or die.

Therefore it is desirable to control the properties of transfusion blood, for example, to limit and/or counteract any deterioration in the properties of transfusion blood during storage, so that the blood provided to the patient is of improved quality.

In a first aspect, the present invention may provide a method of treating blood externally to a human or animal body, the blood having been extracted from a first human or animal body for delivery to a second human or animal body, the method comprising controlling the temperature and/or composition of the blood.

The blood has typically been extracted from the first human or animal body for the purposes of providing a transfusion to the second human or animal body, e.g. to alleviate conditions such as anaemia or acute blood loss in the second human or animal body.

Typically, blood extracted from the first human or animal body must be stored before it can be delivered to the second human or animal body. Therefore, the method generally comprises treating the blood to limit or counteract deterioration of blood during storage In certain examples, the method may comprise controlling the levels of gaseous species (such as oxygen, carbon dioxide, and/or nitric oxide) dissolved in the blood, by increasing or decreasing the level of the gaseous species.

For example, oxygen may be added to the blood to ensure that the blood delivered to the recipient is fully saturated with oxygen (that is, the saturation levels may be greater than 90%, preferably greater than 95%). Additionally or alternatively, oxygen may be added to or removed from the blood to ensure that appropriate levels of oxygen are present during the storage and transportation of blood and red blood cells.

In a further example of the method of the first aspect of the invention, carbon dioxide may be added to or removed from the blood (in general, removed from the blood) to ensure that transfusion blood is delivered to the recipient with appropriate levels of carbon dioxide and/or that appropriate levels of carbon dioxide are present during the storage of blood and red blood cells.

Nitric oxide has been found to play an important role in promoting the ability of blood to transport oxygen. It is generally present in small concentrations in venous blood, but it has been found that these concentrations are reduced during storage of the blood externally to the body. Therefore, nitric oxide may be added to transfusion blood to restore (at least in part) the ability of the blood to carry oxygen. Alternatively, a precursor to nitric oxide may be added that promotes the natural process for nitric oxide generation.

In certain cases, the method may comprise increasing or decreasing the level of ionic species present in the blood, e.g. sodium and/or potassium ions. This may help to ensure an equilibrium between the ion concentrations in red blood cells and the main blood stream, thus limiting diffusion of these ionic species to or away from red blood cells.

In particular cases, it has been found that potassium concentration in stored blood increases to undesirably high levels. Therefore, it is desirable to regulate the potassium concentration of the blood at the time of delivery to the patient. Similar considerations apply to excessive levels of lactate in the blood.

In certain cases, the method may comprise increasing or decreasing (generally increasing) the level of 2,3-diphosphoglycerate (2,3-DPG) in the blood. This compound is known to be important in aiding the release of oxygen molecules from haemoglobin. Alternatively, a precursor to 2,3-DPG may be used that promotes 2,3-DPG production.

The method may comprise any adjustment to the composition of the blood that is required to control the hydrogen ion concentration (pH) of the blood.

The blood may be treated using a mass exchanger, that is, an apparatus providing one or more flow paths along which blood may be passed, to receive or donate chemical species.

Additionally or alternatively, the blood may be treated using a heat exchanger to receive or donate thermal energy.

The mass exchanger may be e.g. a blood/gas mass exchanger in which blood is passed along a first flow path and gas is passed along a second flow path, there being a permeable interface between the first and second flow paths, to allow the transfer of chemical species between the flow paths. The permeable interface may comprise one of silicone, polyphenylene oxide, polymethylpentene and microporous polypropylene.

As an alternative, the mass exchanger may be e.g. a blood/liquid mass exchanger in which blood is passed along a first flow path and liquid (e.g. aqueous liquid) is passed along a second flow path, the interface between the two flow paths allowing the transfer of chemical species therebetween.

The second flow path may be e.g. contained within a tube, while the first flow path passes around the outer surface of the tube. The flow paths may alternatively be passages between planar sheets of selectively permeable materials. Other configurations are also possible.

Typically, a blood/liquid mass exchanger may also serve to regulate the temperature of the blood, e.g. by using treatment liquid that has been heated or cooled to a specified temperature, so that thermal energy is transferred to or from the blood. Alternatively, the treatment liquid may comprise a mixture that reacts to generate or absorb heat, as is known in the art. Typically, blood may be cooled after extraction, to prepare it for storage and/or heated before delivery to the patient.

Blood/gas or blood/liquid mass exchangers may be operated in co-current flow mode, that is, the blood flows in the same direction as the liquid or gas. Co-current flow has the advantage that the blood and the treatment fluid tend to move towards equilibrium with each other as they travel through the mass exchanger, helping to ensure accurate control of the resultant blood composition.

Alternatively, counter-current flow may be employed to enhance the rate of transfer of species between the blood and the treatment fluid.

As an example, counter-current flow may be used to achieve rapid treatment of blood that is intended for storage, while co-current flow may be used to help ensure accurate control of the composition of blood that is being treated for delivery to a recipient body.

Similar considerations apply in the case that blood is being treated in a heat exchanger. For example, if the blood is intended for storage, then it may be desirable to cool it as rapidly as possible, through use of counter-current flow between the blood and the fluid medium in the heat exchanger. Alternatively, if the blood is being prepared for delivery to a recipient body, then it may be desirable to control the blood temperature as accurately as possible, through the use of co-current flow between the blood and the fluid medium in the heat exchanger.

In an alternative example of the first aspect of the invention, the mass exchanger may be a blood/solid mass exchanger, that is, a mass exchanger having at least one channel through which blood is passed, the walls of the channel being configured to add or remove species from the blood.

The use of a mass exchanger may have the advantage of avoiding harsh physical or chemical treatments (e.g. centrifugation) that may damage the blood.

The blood may be treated at the time of extraction from the human or animal body, i.e. prior to storage. Alternatively, the blood may be treated after extraction, during storage. In a further alternative, blood may be treated at the point of delivery to the patient. Additionally, blood may be treated prior to storage and the treatment reversed or altered prior to delivery of the blood to the patient.

In the case that the blood is treated at the time of extraction from the human or animal body, the step of treating the blood preferably takes place less than one minute after the blood has left the body, more preferably less than 30 seconds. It is thought that the initial changes to the blood as it leaves the donor are very rapid. Thus, prompt treatment at the time of extraction of the blood from the body can help to minimise deterioration. In this case, the blood is treated as "whole blood", that is, no separation of the blood into its various constituents is carried out before the start of the treatment (although the blood may later be separated e.g. through centrifugation to remove plasma).

Blood that is treated during storage or at the time of delivery to the human or animal body may be treated in the form of whole blood or in the form of packed red blood cells.

It is particularly desirable to treat blood at the time of delivery to the human or animal body, so as to exert careful control over the quality of blood delivered to the patient. For example, the oxygen level of the blood may be increased e.g. to 95% saturation, or preferably to 99% saturation. In general, it is desirable that the quality of the blood delivered to the patient should be at least as high as the quality of the patient's own arterial blood. However, it may be problematic to deliver blood that is of too high quality relative to the patient's own arterial blood, as this may create a shock to the patient's system.

In cases where a mass exchanger is used, the scale of the mass exchanger may be selected according to the application envisaged. For example, when only a small amount of blood is to be treated and delivered to a patient (e.g. for the treatment of anaemia), a small-scale mass exchanger may be used, the blood being passed through the mass exchanger at a rate of less than 15 ml/min, preferably less than 10 ml/min, more preferably less than 5 ml/min.

When larger amounts of blood are to be treated and delivered to a patient, e.g. to compensate for acute blood loss, a larger-scale mass exchanger may be used, the blood being passed through the mass exchanger at a rate greater than 20 ml/min, preferably greater than 30 ml/min.

In other cases, the blood may be passed through the first flow path at a flow rate between 15 ml/min and 20 ml/min.

The driving force for passing blood through the mass exchanger may be provided e.g. by gravity or a pump. For example, a peristaltic pump may be used. The peristaltic pump may be a two-roller peristaltic pump that is adapted to deliver separate streams of blood and treatment fluid to a blood/gas or blood/liquid mass exchanger. In certain embodiments of the invention, other pump configurations may be preferred.

In other cases, the driving force may be provided by the patient's own venous blood pressure (in the case that the blood is treated at the time of extraction from the patient's body), by gravity, or by controlled squeezing of a blood bag.

In certain cases, the treatment fluid may comprise a first fluid component and a second fluid component, the first and second fluid components having different chemical compositions, the first and second fluid components being mixed before being supplied to the mass exchanger.

For example, the first and second fluid components may be passed through a flow mixer, whereby the fluids are caused to flow along separate flow paths towards a junction, where they become mixed.

In other examples of the invention where it is desired to control the levels of more than one chemical species in the blood, the blood may be treated successively with a plurality of different treatment fluids (that is, the treatment fluids may be applied one after the other). In such cases, different permeable interfaces may be provided between the treatment fluid and the blood, depending on the treatment fluid being used.

In some cases, a plurality of mass exchangers may be provided that are arranged in series. In these cases, the blood is generally caused to flow through each of the mass exchangers in turn, and is treated with a different treatment fluid in each mass exchanger.

Preferably, the surface defining the first flow path is configured to provide a non-thrombogenic or anti-thrombogenic effect.

The mass exchanger may have one or more features of the mass exchanger described in WO 2012/160347, which is hereby incorporated by reference.

In a second aspect, the present invention may provide a method of extracting one or more chemicals from human or animal blood, comprising the steps of:
  providing a mass exchanger, the mass exchanger being configured to provide a first flow path and a second flow path, the first and second flow paths being separated by a permeable interface;
  causing the blood to flow along the first flow path; and
  causing a treatment gas or treatment liquid to flow along the second flow path.

The invention will now be described by way of example with reference to the following Figures in which:

FIG. 1 is a schematic section view of a mass exchanger and associated pump, for use in an example of a method according to the first or second aspect of the invention.

Referring to FIG. 1, a mass exchanger 10 has a treatment fluid inlet 12, a treatment fluid outlet 14, a blood inlet 16 and a blood outlet 18. The treatment fluid inlet 12 and treatment fluid outlet 14 are connected by a plurality of tubes 20 that provide fluid communication between the inlet and outlet. The tubes 20 may be constructed of gas-permeable polymers, such as silicones, polymethylpentene, or polyphenylene oxide, or from microporous materials such as microporous polypropylene.

The blood inlet 16 and blood outlet 18 are connected by the mass exchanger chamber 17, which houses the tubes 20.

A 2-roller peristaltic pump 22 receives treatment fluid through a first inlet 24 and blood through a second inlet 26. The pump 22 delivers the treatment fluid and blood to the treatment fluid inlet 12 and the blood inlet 16 respectively.

When in use, the pump 22 receives blood through the second inlet 26. The blood may flow directly from the donor to the pump, or may have been held in storage. The pump receives treatment fluid through the first inlet 24. The treatment fluid may be a liquid or a gas. The composition of the treatment fluid has typically been chosen to remove or donate particular chemical species from or to the blood, e.g. oxygen, carbon dioxide, and/or sodium or potassium ions. The treatment fluid may also have been heated or cooled to a particular temperature, in order to deliver or remove thermal energy to or from the blood.

The pump delivers treatment fluid to the respective inlet 12 of the mass exchanger through the action of a first roller (not shown). Blood is delivered to the respective inlet 16 of the mass exchanger through the action of a second roller (not shown). The first and second rollers may be operated independently to give the required flow rates of treatment fluid and blood through the mass exchanger 10. Alternatively, the relative size of the tubes and/or rollers in the pump may be selected to give a desired relative flow rate between the blood and the treatment fluid.

The treatment fluid flows from the inlet 12 to the outlet 14 via the tubes 20. Blood flows through the mass exchanger chamber 17, from the inlet 16 to the outlet 18, around the outer surfaces of the tubes 20. Due to the permeable nature of the tube walls, chemical species diffuse across the walls of the tubes 20, from the treatment fluid to the blood, or vice versa. The nature of the chemical species diffusing across the tube walls depends on the composition of the treatment fluid and the blood. The walls of the tubes 20 may also conduct heat to or from the blood.

The blood flow rate through the mass exchanger 10 may vary from 4 ml/min (e.g. for treating anaemia) to 30 ml/min (e.g. for compensating for acute blood loss in a patient).

In alternative examples of the method of the invention, in which blood is treated at the time of extraction from the human or animal body, the blood is driven through the mass exchanger by the venous blood pressure of the body. In such cases, the blood flow rate through the mass exchanger generally ranges from 40 ml/min to 90 ml/min and the flow rate of the treatment fluid is adjusted accordingly.

In further alternative examples of the invention, in which blood is treated at the time of delivery to the human or animal body, the blood may be driven through the mass exchanger through the action of gravity, rather than by a pump. As an alternative, a blood bag may be squeezed in a controlled manner.

Blood leaving the blood outlet 18 may be delivered directly to the patient, placed in storage, or further treated. Treatment fluid may be subjected to further treatment to isolate useful chemicals that have been extracted from the blood.

In the case that blood is treated at the time of extraction from the human or animal body, the treatment generally comprises action to prolong the storage life of the venous blood, for example, by greatly reducing oxygen concentration and/or cooling the blood.

In the case the blood is treated at the time of delivery to the human or animal body, the blood may be treated to give properties comparable with well-oxygenated arterial blood. In this way, the blood is immediately capable of delivering oxygen to the tissues of the patient. Even if the treatment does not fully restore the ability of the transfused blood to transport oxygen, it will deliver oxygen to the patient throughout the transfusion.

The invention claimed is:

1. A method of transfusing blood into a patient, comprising:
    connecting at least one mass exchanger directly to the patient at a point of delivery to the patient;
    connecting a source of blood to the mass exchanger, the blood having been extracted from a donor for delivery to the patient, the blood having a first level of at least one of temperature and dissolved oxygen;
    changing at least one of temperature and dissolved oxygen of the blood to a second level having a relatively greater therapeutic value than the first level by running the blood through the mass exchanger while delivering the blood directly to the patient at a point of delivery to the patient, the changing carried out at a rate corresponding to a therapeutic rate of blood entry corresponding to the amount of blood to be delivered.

2. The method according to claim 1, further comprising treating the blood during storage, prior to delivery to the patient.

3. The method according to claim 1, further comprising changing the composition of the blood prior to or during storage of the blood.

4. The method according to claim 1, wherein changing further includes increasing or decreasing levels of gaseous species dissolved in the blood other than oxygen.

5. The method according to claim 4, wherein the gaseous species comprises one or more of carbon dioxide and nitric oxide.

6. The method according to claim 1, wherein changing further includes increasing or decreasing levels of ionic species in the blood.

7. The method according to claim 6, wherein the ionic species comprises one or more of sodium ions, potassium ions, and lactate ions.

8. The method according to claim 1, wherein changing further includes increasing levels of 2,3-diphosphoglycerate.

9. The method according to claim 1, wherein changing further includes adjusting hydrogen ion concentration (pH) of the blood.

10. The method according to claim 1, wherein a changed level of dissolved oxygen is greater than 95% of saturation of the blood.

11. The method according to claim 1, wherein the mass exchanger has at least one channel defining a second flow path for a treatment fluid and bound by walls configured to donate or absorb a predetermined chemical species to or from blood flowing outside the channel.

12. The method according to claim 1, wherein at least dissolved oxygen is changed, and changing includes delivering the blood to a first flow path of the mass exchanger and delivering a treatment fluid to a second flow path of the mass exchanger, wherein the blood flows along the first flow path and the treatment fluid flows along the second flow path separated by a permeable interface in the mass exchanger.

13. The method according to claim 12, further comprising, prior to delivery to the second flow path, mixing a first fluid component of a treatment fluid together with a second fluid component of a treatment fluid, the first and second fluid components having different chemical compositions.

14. The method according to claim 12, further comprising:
providing a second mass exchanger also connected to the IV line inserted into a blood vessel of the patient; and
delivering a treatment fluid to a flow path of the second mass exchanger; wherein the blood is treated with a different treatment fluid in each mass exchanger.

15. The method according to claim 1, wherein the blood is whole blood or packed red blood cells.

16. A method of extracting one or more chemicals from human or animal blood to be delivered to a patient, the method comprising:
providing a mass exchanger, the mass exchanger having a first flow path and a second flow path separated by a permeable interface;
connecting the mass exchanger directly to the patient through an IV line at a point of delivery to the patient;
delivering the blood to the first flow path, whereupon the blood flows along the first flow path;
delivering a treatment fluid which is a liquid or gas for extracting one or more chemicals from the blood to the second flow path, whereupon the treatment gas or liquid flows along the second flow path;
extracting the one or more chemicals from the blood through the permeable interface at a rate corresponding to a therapeutic rate of blood entry corresponding to the amount of blood to be delivered; and
delivering the blood treated by the treatment fluid to the patient at a therapeutic rate.

17. The method according to claim 16, wherein the treatment fluid is a liquid or a gas.

18. The method according to claim 16, wherein the permeable interface comprises one of a silicone, polyphenylene oxide, polymethylpentene, and microporous polypropylene.

19. The method according to claim 16, wherein the treatment fluid is a water-based liquid.

20. The method according to claim 16, wherein the blood and the treatment fluid flow through the mass exchanger in one of a same direction and an opposite direction.

21. The method according to claim 16, further comprising controlling temperature of the treatment fluid to warm or cool the blood.

22. The method according to claim 16, wherein, upon delivery to the first flow path, the blood passes through the first flow path at a flow rate less than 15 ml/min.

23. The method according to claim 16, wherein, upon delivery to the first flow path, the blood passes through the first flow path at a rate between 15 ml/min and 20 ml/min.

24. The method according to claim 16, wherein blood passes through the first flow path by at least one of action of gravity and by action of a pump.

25. The method according to claim 24, wherein blood passes through the first flow path by action of a peristaltic pump.

26. The method according to claim 25, wherein the treatment gas or treatment liquid passes through the second flow path by action of the peristaltic pump and wherein the blood and treatment gas or treatment liquid are metered in proportion.

27. The method according to claim 16, comprising delivering a plurality of treatment fluids to the second flow path in succession.

28. The method according to claim 16, wherein a surface defining the first flow path has a non-thrombogenic or anti-thrombogenic effect.

29. The method according to claim 16, further comprising treating the blood at extraction from the human or animal body.

30. The method according to claim 29, wherein the treating limits or counteracts deterioration of the blood during storage.

31. The method according to claim 16, further including changing the temperature of the blood to a predetermined temperature at a rate corresponding to a rate of blood entry into the patient through the IV line.

32. The method according to claim 16, wherein the flow rate of blood into the patient through the IV line is less than 10 ml/min.

33. The method according to claim 16, further including a peristaltic pump operatively connected to the mass exchanger and IV line.

34. A method of transfusing blood into a patient, comprising:
connecting at least one mass exchanger directly to the patient at a point of delivery to the patient, the mass exchanger having first and second flow paths;
connecting a source of blood to the mass exchanger to be admitted into the first flow path, the blood having been extracted from a donor for delivery to the patient, the blood having a first level of at least one of temperature and dissolved oxygen;
connecting a source of treatment fluid to the second flow path;
changing at least one of temperature and dissolved oxygen of the blood to a second level having a relatively greater therapeutic value than the first level by running the blood and treatment fluid through the mass exchanger to the patient directly at a point of delivery to the patient, the changing carried out at a rate corresponding to the rate of blood entry into the patient.

* * * * *